United States Patent
Brown et al.

(10) Patent No.: US 8,337,816 B2
(45) Date of Patent: Dec. 25, 2012

(54) DRY POWDER MEDICAMENT FORMULATIONS

(75) Inventors: Andrew Bruce Brown, Durham, NC (US); Michael Mary Van Oort, Durham, NC (US)

(73) Assignee: Glaxo Group Limited, Greenforo, Middlesex (GB)

( * ) Notice: Subject to any disclaimer, the term of this patent is extended or adjusted under 35 U.S.C. 154(b) by 1931 days.

(21) Appl. No.: 10/489,491

(22) PCT Filed: Sep. 16, 2002

(86) PCT No.: PCT/US02/29267
§ 371 (c)(1),
(2), (4) Date: Mar. 12, 2004

(87) PCT Pub. No.: WO03/024396
PCT Pub. Date: Mar. 27, 2003

(65) Prior Publication Data
US 2004/0241232 A1    Dec. 2, 2004

Related U.S. Application Data

(60) Provisional application No. 60/322,783, filed on Sep. 17, 2001.

(51) Int. Cl.
*A61K 9/00* (2006.01)
*A61K 9/14* (2006.01)
*A61K 9/16* (2006.01)
(52) U.S. Cl. .......................... 424/46; 424/489
(58) Field of Classification Search ............. 424/489, 424/499, 501, 46; 514/951, 952
See application file for complete search history.

(56) References Cited

U.S. PATENT DOCUMENTS

| | | | |
|---|---|---|---|
| 5,202,309 A | 4/1993 | Schwartz et al. | |
| 5,478,578 A * | 12/1995 | Arnold et al. | 424/499 |
| 5,641,510 A | 6/1997 | Clark et al. | |
| 6,309,623 B1 * | 10/2001 | Weers et al. | 424/45 |
| 6,559,293 B1 | 5/2003 | Almarsson et al. | |
| 6,576,793 B1 | 6/2003 | Moran et al. | |
| 6,645,466 B1 * | 11/2003 | Keller et al. | 424/43 |
| 6,737,044 B1 * | 5/2004 | Dickinson et al. | 424/46 |
| 7,541,022 B2 * | 6/2009 | Staniforth et al. | 424/46 |
| 7,678,364 B2 * | 3/2010 | Edwards et al. | 424/46 |

(Continued)

FOREIGN PATENT DOCUMENTS
EP    0069715    1/1983
(Continued)

OTHER PUBLICATIONS

Merriam-Webster's Collegiate Dictionary, 1996, Tenth Edition, 3 Page.*

(Continued)

*Primary Examiner* — James H. Alstrum-Acevedo
(74) *Attorney, Agent, or Firm* — Robert J. Smith (57) ABSTRACT

A dry powder pharmaceutical composition comprising (i) a medicament particle fraction comprising medicament particles with an aerodynamic diameter no greater than 10 μm; and (ii) at least 50% of a non-respirable excipient fraction comprising low density excipient particles with an aerodynamic diameter greater than 10 μm and a geometric diameter greater than 30 μm. In additional embodiments of the invention, the pharmaceutical composition includes a respirable excipient fraction comprising excipient particles with an aerodynamic diameter no greater than 10 μm. In a preferred embodiment of the invention, the non-respirable excipient particles include pores adapted to receive a portion of the respirable excipient fraction and/or the medicament fraction.

7 Claims, 2 Drawing Sheets

U.S. PATENT DOCUMENTS

| | | | |
|---|---|---|---|
| 2002/0141946 A1* | 10/2002 | Schmitke et al. | 424/46 |
| 2003/0162835 A1 | 8/2003 | Staniforth et al. | |
| 2003/0185764 A1 | 10/2003 | Staniforth et al. | |
| 2004/0101483 A1 | 5/2004 | Muller-Walz et al. | |
| 2006/0165606 A1* | 7/2006 | Tarara et al. | 424/46 |
| 2006/0239932 A1 | 10/2006 | Monteith et al. | |

FOREIGN PATENT DOCUMENTS

| | | |
|---|---|---|
| EP | 0237507 | 9/1987 |
| GB | 2064336 | 6/1981 |
| GB | 2129691 | 5/1984 |
| GB | 2178965 | 2/1987 |
| GB | 2242134 | 9/1991 |
| WO | 8705213 | 9/1987 |
| WO | 9623485 | 8/1996 |
| WO | 9913867 | 3/1999 |
| WO | 0028979 | 5/2000 |
| WO | 0053157 | 9/2000 |
| WO | 0053158 | 9/2000 |
| WO | 0105429 | 1/2001 |
| WO | 0142193 | 6/2001 |
| WO | 0178693 | 10/2001 |
| WO | 0178694 | 10/2001 |
| WO | 0178695 | 10/2001 |
| WO | 02070490 | 9/2002 |
| WO | 02076933 | 10/2002 |
| WO | 02078671 | 10/2002 |
| WO | 03007919 | 1/2003 |
| WO | 03024396 | 3/2003 |
| WO | 03024439 | 3/2003 |
| WO | 03057194 | 7/2003 |
| WO | 03072539 | 9/2003 |
| WO | 03088943 | 10/2003 |
| WO | 03088944 | 10/2003 |
| WO | 03091204 | 11/2003 |
| WO | 2004016578 | 2/2004 |
| WO | 2004022547 | 3/2004 |
| WO | 2004037768 | 5/2004 |
| WO | 2004037773 | 5/2004 |
| WO | 2004037807 | 5/2004 |
| WO | 2004039762 | 5/2004 |
| WO | 2004039766 | 5/2004 |
| WO | 2005004845 | 1/2005 |
| WO | 2005004852 | 1/2005 |

OTHER PUBLICATIONS

"Porosimetry," accessed on Mar. 3, 2012 at en.wikipedia.org/wiki/Porosimetry.*

Wirth, et al., "Maillard Reaction of Lactose and Fluoxetin Hydrochoride, A Secondary Amine" J. of Pharm. Sciences, 1998, vol. 87(1), pp. 31-39.

Hammouda, et al., "Lactose-induced Discoloration of Amino Drugs in Solid Dosage Form" Kurze Originalmitteilungen, 1970, vol. 25, pp. 181.

Kumar, et al., "Maillard Reaction and Drug Stability" Royal Soc. of Chemistry, 1999, vol. 151, pp. 20-27.

Zeng, et al., "The role of fine particle lactose on the dispersion and deaggregation of salbutamol sulphate in an air stream in vitro" Intl J. of Pharmaceutics, 1998, vol. 176, pp. 99-110.

U.S. Appl. No. 10/473,874, filed as the English-language equivalent of WO02/078671.

* cited by examiner

DRY POWDER MEDICAMENT FORMULATIONS

This application is filed pursuant to 35 USC 371 as a United States National Phase Application of International Patent Application Serial No. PCT/US02/29267 filed on 16 Sep. 2002, which claims priority from U.S. Provisional Application 60/322,783 filed on 17 Sep. 2001 in the United States.

TECHNICAL FIELD OF THE INVENTION

The present invention relates generally to pharmaceutical compositions. More particularly, the invention relates to inhalable dry powder medicament formulations and pharmaceutical compositions for delivery of one or more medicaments to the pulmonary system.

BACKGROUND OF THE INVENTION

Pharmaceutical compositions may advantageously be administered by inhalation to or through the lung of a patient. In inhalation therapy, a pharmaceutical delivery device, such as a dry powder inhaler ("DPI"), is typically employed to deliver a prescribed dose of a pharmaceutical composition and, hence, medicament to the pulmonary system of a patient. As is well known in the art, in a typical DPI, a dose of the pharmaceutical composition is positioned in an aerosolization chamber, where it is aerosolized and, hence, dispersed into respirable particles by airflow supplied by a pressurized source of gas or by the patient's inspiration effort. It is also well known in the art that in order to settle in the appropriate regions of the lung associated with local and/or systemic drug delivery, the dispersed particles must be of suitable size.

The pulmonary system includes the upper airways, including the oropharynx and larynx, followed by the lower airways, which include the trachea followed by bifurcations into bronchi and bronchioli. The upper and lower airways are called the conducting airways. The terminal bronchioli then divide into respiratory bronchioli, which then lead to the alveolar region, or the deep lung. See, Gonda, I, "Aerosols for Delivery of Therapeutic and Diagnostic Agents to the Respiratory Tract", *Critical Reviews in Therapeutic Drug Carrier Systems*, vol. 6, pp. 273-313 (1990).

The smooth muscle regions of the conducting airways, and particularly the lower airways, possess receptors (i.e., protein based, macromolecular complexes existing within cell membranes which, upon interaction with specific agents, change conformation and lead to the triggering of a cellular response, such as smooth muscle cell contraction or relaxation) that are the primary target site of local medicament particle delivery. The alveolar region of the deep lung, although it too may possess receptors effecting local response, is the target site for pulmonary systemic delivery, as the alveoli provide access to vascular system through a closely associated vascular capillary network.

It is well known that medicament particles deposit in specific areas of the pulmonary system based upon the aerodynamic size of the particles and the flow rate of the fluid within which they are entrained. Typically, with average inhalation flow rates of between 10 and 60 liters per minute, particles having an aerodynamic diameter in the range of 0.5 to 3 μm are suitable for systemic delivery, as these particles deposit selectively in the deep lung. Particles having an aerodynamic diameter in the range of approximately 0.5 to 10 μm, preferably, 1 to 6 μm, and more preferably, 3 to 6 μm are suitable for local lung delivery, as they will deposit in the conductive airways.

Particles having an aerodynamic diameter greater than 10 μm generally deposit in the mouth, throat or upper airways, offering little therapeutic benefit. Particles having an aerodynamic diameter less than 0.5 μm do not settle out of the air flow to deposit in the lungs, and are subsequently respired when the patient exhales.

The effectiveness of dry powder pharmaceutical composition delivery depends upon the ability to precisely and reproducibly meter small quantities of medicament into doses. The metering is typically achieved by diluting the medicament in a pharmaceutical composition containing one or more excipients. The pharmaceutical composition can then be metered with a greater margin of error than a highly potent medicament alone.

The pharmaceutical composition should be sufficiently flowable to permit the composition to be poured or otherwise transferred into individual doses. Measures of flowability are typically quantified by the compressibility of the powder composition, as well as its "angle of repose." Measurement of these features may be made using standardized methodologies known in the art.

Compositions are also advantageously highly aerosolizable, to clear the composition from the inhaler device. The composition is preferably dispersible into particles of respirable size. Measurements of aerosolizibility and dispersiblity may be made by measuring the emitted dose and fine particle fraction of the composition, respectively, using methodologies known to the art. A common device used in measuring fine particle fraction is an Anderson Cascade Impactor.

Efforts in the area of meterability have long included the use of excipients, such as milled or micronized lactose, to dilute the medicament in the pharmaceutical composition, allowing microgram quantities of very potent medicaments to be precisely metered into milligram sized doses with an acceptable degree of control. By controlling the size ranges of the excipient powders, gains have been reported in flowability, dispersability and aerosolization of dry powder medicament formulations.

For example, in EP 0,663,815 an excipient powder is disclosed for use with an inhalable micronized medicament that has coarse and fine excipient fractions. The coarse fraction improves aerosolibility (i.e., emitted dose), while the fine fraction improves dispersability (i.e., measured as fine particle fraction). The coarse excipient fraction (i.e., mill ground) has an average particle size of at least 20 μm. The fine excipient fraction has an average particle size no greater than 10 μm. Similarly, the medicament has a particle size no greater than 10 μm.

In PCT Publication WO 00/33789 an excipient powder is disclosed comprising a coarse first fraction of which at least 80% by weight has a particle size of at least 10 μm; a fine second fraction which at least 90% by weight has a particle size of no greater than 10 μm; and a third fraction consisting of a ternary agent. Preferably, the ternary agent is provided in an additional fine (i.e., 10 μm or less) fraction, but slightly larger sizes are acceptable. The disclosed suitable ternary agents include water soluble and physiologically acceptable materials, i.e., water surface active or amino acids, peptides and polypeptides or derivatives thereof, with the preferred ternary agent being L-leucine. According to WO 00/33789, particles with a diameter in the range of 10 to 30 μm have an adverse effect on powder flow characteristics without imparting any benefit of medicament delivery (i.e., dispersion).

In an effort to increase the aerodynamic properties (aerosolizibility and dispersability) of the particles delivered to the selected target region of the lungs, recent efforts have led to a departure from the use of medicament particles milled to respirable size and then blended with excipient carriers. The new approach appears to be the use of respirable engineered particle compositions have morphologies and physical and chemical attributes with allegedly superior aerodynamic characteristics. These particles may be hollow or porous, and have a range of particle densities, all providing better aerosolization characteristics.

For example, according to WO 99/16419, prior art compositions containing milled respirable drug particles and large excipient carrier particle systems may allow for at least some medicament particles to loosely bind to the surface of the large carrier surface and disengage upon inhalation, but a substantial amount of the medicament fails to disengage from the large lactose particles and is deposited in the throat. To allow undesirable throat deposition to be reduced, PCT Patent Publication WO 99/16419 discloses microporous microparticles containing a medicament, an excipient (i.e., lactose) and surfactant. The microporous nature of these particles purportedly provides superior aerodynamic characteristics, allowing particle-to-particle aggregation to be overcome without the use of large excipient particles. This advance allows the large excipient carriers particles to be eliminated from the formulation altogether.

Similar to the microporous microparticles disclosed in WO 99/16419, U.S. Pat. No. 5,993,805 discloses smooth, spherical, solid walled, hollow microparticles (1 to 10 μm in size) that are intended for aerosolized medicament delivery to the lung(s). This reference similarly does not address the use of large excipient particles.

U.S. Pat. Nos. 5,874,064, 5,855,913 and 5,985,309, which are incorporated by reference herein, disclose low density particle compositions that can be readily entrained into the inhalation path of a patient and deposited into the desired areas of the lungs of a patient to effectuate local or systemic delivery. The particle compositions have a tap density less than 0.4 g/cm$^3$ and a mass mean diameter in the range of 5 to 30 μm to yield an aerodynamic diameter of 1 to 5 μm. The medicament is adsorbed, absorbed, or otherwise incorporated onto or into the matrix of low-density particles. Advantageously, but optionally, these low-density particles are deliverable with larger carrier particles having no medicament, but a mean diameter in the range of 50 to 100 μm. No other mention is made of attributes of the large carrier particles in question.

Progress in the art of dry powder pharmaceutical compositions, in terms of meterability, flowability, dispersiblity and aerosolibility remains desirable. Micronized medicament/excipient blends are encumbered to a certain degree by their inherent aerodynamic attributes. Thus, achieving very high degrees of aerosolibility and dispersiblity using micronized excipients is somewhat limited by these attributes.

Modification of the physical structure of the particles incorporating the medicament or bioactive agent via particle engineering is also often difficult or impossible due to the physical and chemical properties of the active agent itself. Indeed, it is well known that not all medicaments (or bioactive agents) can be incorporated in a particle matrix to provide desired aerodynamic properties suitable for inhalation. Limitations also exist in the ability to incorporate specific concentrations, such as very high or low concentrations, of certain medicaments into suitable matrix forms.

Thus, there exists a need to provide a pharmaceutical composition suitable for delivery of medicaments that have a high degree of aerosolibility and dispersability. There also exists a need for a pharmaceutical composition that does not depend on the capability of a medicament to be able to form a medicament-excipient matrix, which matrix is delivered to the target sites in the lung to be released for local and/or systemic delivery. Additionally, there exists a need to provide pharmaceutical compositions with increased stability, whereby the aerosolization and dispersion characteristics of the composition can be maintained throughout a given shelf life without giving an inconsistent therapeutic or delivery profile.

It is therefore an object of the present invention to provide a novel dry powder pharmaceutical composition having improved meterability, flowability, dispersability and/or aerosolibility.

It is another object of the present invention to provide a dry powder pharmaceutical composition including excipient particles having one or more of such improved properties.

It is another object of the present invention to provide a pharmaceutical composition that is not dependent on a given medicament's ability to be formed into a matrix particle of medicament and excipient.

It is yet another object of the present invention to provide pharmaceutical compositions having improved physical and/or chemical stability.

SUMMARY OF THE INVENTION

In accordance with the above objects and those that will become apparent below, the dry powder pharmaceutical composition in accordance with this invention generally comprises (i) a medicament fraction comprising medicament particles with an aerodynamic diameter no greater than 10 μm; and (ii) at least 50% of a non-respirable excipient fraction comprising excipient particles with an aerodynamic diameter greater than 10 μm and a geometric diameter greater than 30 μm.

In additional embodiments of the invention, the pharmaceutical composition includes a respirable excipient fraction comprising excipient particles with an aerodynamic diameter no greater than 10 μm.

In a preferred embodiment of the invention, the non-respirable excipient particles have sufficient porosity (i.e., defining pores) to receive a portion of the respirable excipient fraction and/or the medicament fraction.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE INVENTION

Before describing the present invention in detail, it is to be understood that this invention is not limited to particularly exemplified compositions or process parameters as such may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety.

It must be noted that, as used in this specification and the appended claims, the singular forms "a," "an" and "the" include plural referents unless the content clearly dictates otherwise. Thus, for example, reference to "a reagent" includes a mixture of two or more such reagents, reference to "an organic solvent" includes mixtures of two or more such solvents, and the like.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In describing the present invention, the following terms will be employed, and are intended to be defined as indicated below.

DEFINITIONS

By the term "medicament", as used herein, is meant to mean and include any substance (i.e., compound or composition of matter) which, when administered to an organism (human or animal) induces a desired pharmacologic and/or physiologic effect by local and/or systemic action. The term therefore encompasses substances traditionally regarded as actives, drugs and bioactive agents, as well as biopharmaceuticals (e.g., peptides, hormones, nucleic acids, gene constructs, etc.), including, but not limited to, analgesics, e.g., codeine, dihydromorphine, ergotamine, fentanyl or morphine; anginal preparations, e.g., diltiazem; antiallergics, e.g., cromoglycate (e.g., as the sodium salt), ketotifen or nedocromil (e.g., as the sodium salt); antiinfectives, e.g., cephalosporins, penicillins, streptomycin, sulphonamides, tetracyclines and pentamidine; antihistamines, e.g., methapyrilene; anti-inflammatories, e.g., beclomethasone (e.g., as the dipropionate ester), fluticasone (e.g., as the propionate ester), flunisolide, budesonide, rofleponide, mometasone (e.g., as the furoate ester), ciclesonide, triamcinolone (e.g., as the acetonide) or 6α,9α-difluoro-11β-hydroxy-16α-methyl-3-oxo-17α-propionyloxy-androsta-1,4-diene-17β-carbothioic acid S-(2-oxo-tetrahydro-furan-3-yl) ester; antitussives, e.g., noscapine; bronchodilators, e.g., albuterol (e.g., as free base or sulfate), salmeterol (e.g., as xinafoate), ephedrine, adrenaline, fenoterol (e.g., as hydrobromide), formoterol (e.g. as fumarate), isoprenaline, metaproterenol, phenylephrine, phenylpropanolamine, pirbuterol (e.g., as acetate), reproterol (e.g., as hydrochloride), rimiterol, terbutaline (e.g., as sulfate), isoetharine, tulobuterol or 4-hydroxy-7-[2-[[2-[[3-(2-phenylethoxy) propyl]sulfonyl]ethyl]amino]ethyl-2(3H)-benzothiazolone; adenosine 2a agonists, e.g., (2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g., as maleate); $\alpha_4$ integrin inhibitors e.g. (2S)-3-[4-({[4-(aminocarbonyl)-1-piperidinyl]carbonyl}oxy)phenyl]-2-[((2S)-4-methyl-2-{[2-(2-methylphenoxy)acetyl]amino}pentanoyl)amino]propanoic acid (e.g., as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon. The noted medicaments may also be employed in the form of salts, (e.g., as alkali metal or amine salts or as acid addition salts) or as esters (e.g., lower alkyl esters) or as solvates (e.g., hydrates) to optimize the activity and/or stability of the medicament.

The term "medicament" further includes formulations containing combinations of active ingredients, including, but not limited to, salbutamol (e.g., as the free base or the sulfate salt) or salmeterol (e.g., as the xinafoate salt) or formoterol (e.g., as the fumarate salt) in combination with an anti-inflammatory steroid such as a beclomethasone ester (e.g., the dipropionate), a fluticasone ester (e.g., the propionate), a furoate ester or budesonide.

By the terms "medicament formulation" and "pharmaceutical composition", as used herein, it is meant to mean a combination of at least one medicament and one or more added components or elements, such as an "excipient" or "carrier." As will be appreciated by one having ordinary skill in the art, the terms "excipient" and "carrier" generally refer to substantially inert materials that are nontoxic and do not interact with other components of the composition in a deleterious manner. Examples of normally employed "excipients," include pharmaceutical grades of carbohydrates including monosaccharides, disaccharides, cyclodextrins and polysaccharides (e.g., dextrose, sucrose, lactose, raffinose, mannitol, sorbitol, inositol, dextrins and maltodextrins); starch; cellulose; salts (e.g., sodium or calcium phosphates, calcium sulfate, magnesium sulfate); citric acid; tartaric acid; glycine; leucine; high molecular weight polyethylene glyols (PEG); pluronics; surfactants; lubricants; stearates and their salts or esters (e.g., magnesium stearate, calcium stearate); amino acids; fatty acids; and combinations thereof. Examples of suitable "carriers" include water, silicone, gelatin, waxes, and like materials.

By the term "$D_{50}$", as used herein, it is meant to mean the average geometric diameter (i.e., particle size).

By the term "pharmaceutical delivery device", as used herein, it is meant to mean a device that is adapted to administer a controlled amount of a composition to a patient, including, but not limited to, the Diskus® device disclosed in U.S. Pat. Nos. 5,590,654, 5,860,419; 5,837,630, 6,032,666, and U.S. Design Pat. No. 342,994; the Diskhaler™ device disclosed in U.S. Pat. Nos. 4,627,432, 4,811,731, and U.S. Design Pat. No. 299,066; the Rotohaler™ device disclosed in U.S. Pat. No. 4,778,054; the Cyclohaler™ device by Norvartis; the Turbohaler™ device by Astra Zeneca; the Twisthaler™ device by Scheling Plough; the Handihaler™ device by Boehringer Engelheim; the Airmax™ device by Baker-Norton; and the Dura and Inhaled Therapeutic active delivery systems, which are incorporated by reference herein.

As will be appreciated by one having ordinary skill in the art, the present invention substantially reduces or eliminates the disadvantages and drawbacks associated with conventional dry powder pharmaceutical compositions and methods for producing same. As discussed in detail herein, the unique pharmaceutical compositions can be readily employed to provide controlled systemic or local medicament delivery to the pulmonary system via aerosolization.

The pharmaceutical compositions, in accordance with the invention, include a medicament fraction and at least 50% of a non-respirable excipient fraction. The medicament fraction preferably comprises medicament particles having an aerodynamic diameter no greater than 10 μm. The non-respirable excipient fraction preferably comprises excipient particles having an aerodynamic diameter greater than 10 μm and a geometric diameter greater than 30 μm.

According to the invention, the non-respirable excipient particles are also preferably "low density." By the term "low density", as used herein, it is meant to mean particles having a density less than 1 g/cm³.

Accordingly, in one embodiment of the invention, the non-respirable excipient particles have a tap density less than 0.8 g/cm³. In an alternative embodiment of the invention, the non-respirable excipient particles have a tap density in the range of approximately 0.4-0.8 g/cm³.

In additional embodiments of the invention, the pharmaceutical compositions include a respirable excipient fraction comprising excipient particles with an aerodynamic diameter no greater than 10 µm.

Figure 1:
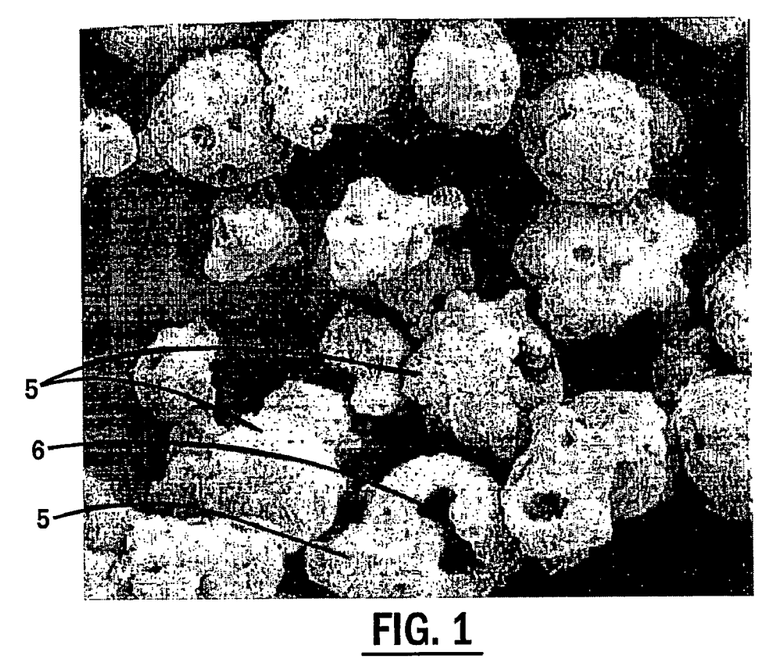
FIG. 1 is an electron micrograph (i.e., SEM) of a porous non-respirable particle according to the invention.
Figure 2:
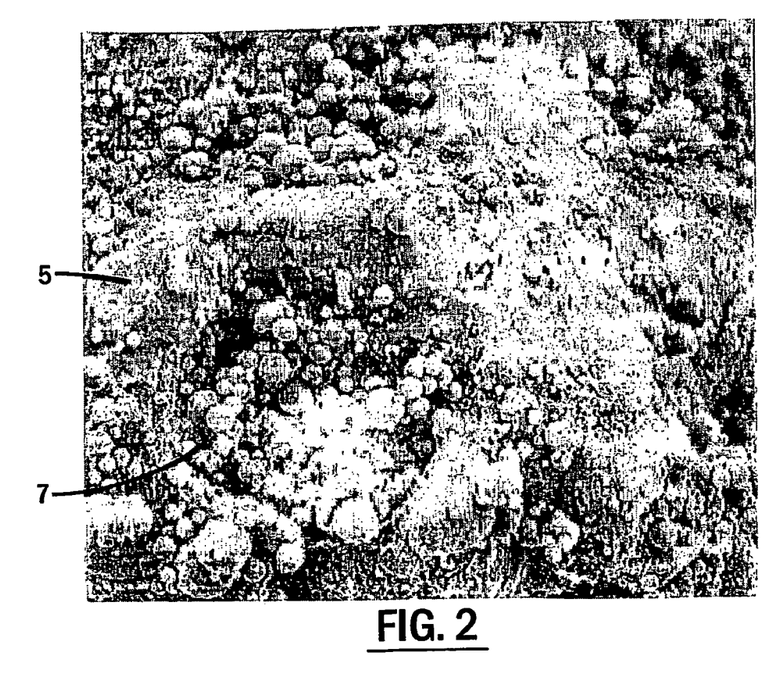
FIG. 2 is an electron micrograph of a porous non-respirable particle having respirable particles disposed in defining pores of the non-respirable particle according to the invention.
Figure 3:
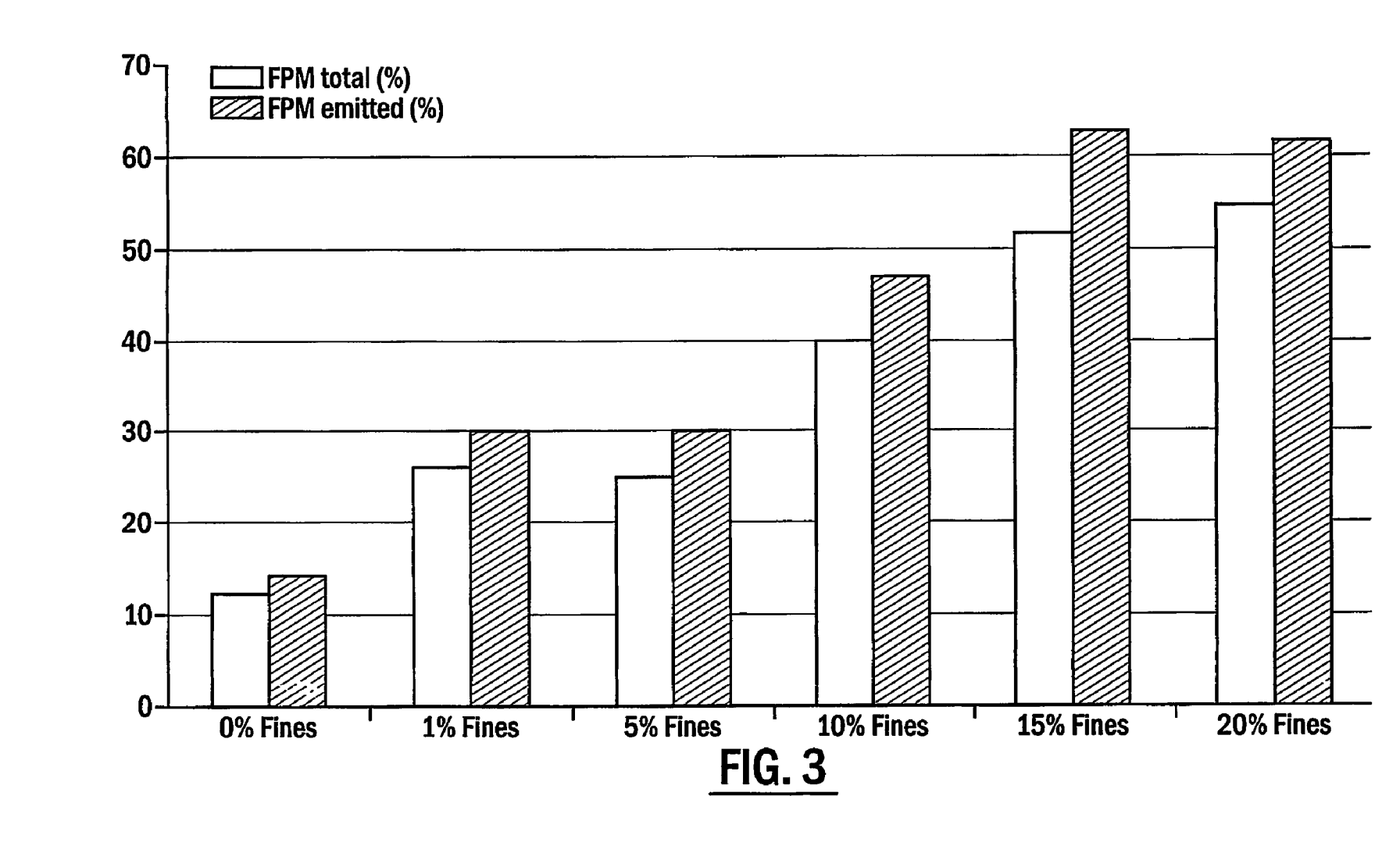
FIG. 3 is a graphical illustration of the effects of fines content on the fine particle mass (FPM) performance according to the invention.

Referring to FIGS. 1 and 2, in a preferred embodiment of the invention, the non-respirable excipient particles 5 have sufficient porosity (i.e., "defining pores", designated 6 in FIG. 1) to receive a portion of the respirable excipient fraction and/or the medicament fraction (designated generally 7 in FIG. 2).

In an alternative embodiment, the non-respirable excipient particles may contain fissures that are adapted, similar to the depicted porous particles, to releasably receive a portion of the respirable excipient fraction and/or medicament fraction. In a further alternative embodiment of the invention, the non-respirable excipient particles may be solid walled, with a smooth or dimpled exterior surface, and may contain an internal void (i.e. one or more hollow cavities) and the medicament fraction and optionally, the respirable excipient fraction, may be releasably carried on the external surface of the carrier.

As will be appreciated by one having ordinary skill in the art, the unique pharmaceutical compositions of the invention provide major advantages over comparable formulations. Among the advantages are enhanced FPM performance, flow characteristics and stability. The medicament concentration and fill weight can also be selected to deliver the desired amount of medicament to the lung.

As discussed in detail herein, various features of the excipient particles, such as surface texture and porosity, directly contribute to the aforementioned advantages. For example, it is well known that porous particles with a relatively large geometric diameter are particularly suitable for inhalation therapy. Due to their relatively large geometric diameter, porous particles exhibit better flow characteristics. Porous particles also have a much higher specific surface area than non-porous particles. Thus, dissolution of the medicament from such particles is faster than from non-porous particles.

Applicants have further found that porous excipient particles can readily be produced such that the porous particles have sufficient porosity to receive a portion of the respirable (i.e., micronized) excipient fraction or medicament fraction (see FIG. 2). As illustrated in FIG. 3, the use of such excipient particles allows a greater percentage of respirable excipient particles (i.e., fines) to be employed (in a low shear blending operation), resulting in enhanced FPM performance without adverse impact on the flow characteristics.

Each fraction of the unique pharmaceutical compositions of the invention will now be discussed in detail.

Medicament Fraction

According to the invention, the medicament fraction comprises at least one of the aforementioned medicaments. In a preferred embodiment of the invention, the medicament fraction comprises at least one of the following medicaments: codeine, dihydromorphine, ergotamine, fentanyl, morphine, diltiazem, cromoglycate, ketotifen, nedocromil; cephalosporins, penicillins, streptomycin, sulphonamides, tetracyclines pentamidine; methapyrilene, beclomethasone, fluticasone, flunisolide, budesonide, rofleponide, mometasone, ciclesonide, triamcinolone, noscapine, albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol or 4-hydroxy-7-[2-[[2-[[3-(2-phenylethoxy) propyl]sulfonyl]ethyl]amino]ethyl-2(3H)-benzothiazolone, 2R,3R,4S,5R)-2-[6-Amino-2-(1S-hydroxymethyl-2-phenylethylamino)-purin-9-yl]-5-(2-ethyl-2H-tetrazol-5-yl)-tetrahydro-furan-3,4-diol, (2S)-3-[4-({[4-(aminocarbonyl)-1-piperidinyl]carbonyl}oxy)phenyl]-2-[((2S)-4-methyl-2-{[2-(2-methylphenoxy) acetyl]amino}pentanoyl)amino] propanoic acid, amiloride; ipratropium, tiotropium, atropine, oxitropium; cortisone, hydrocortisone, prednisolone, aminophylline, choline theophyllinate, lysine theophyllinate, theophylline, insulin or glucagon, and salts, esters and derivatives thereof.

In an additional embodiment of the invention, the medicament fraction most preferably comprises fluticasone, fluticasone propionate or fluticasone furoate. In another embodiment, the medicament fraction comprises salmeterol or salmeterol xinafoate. In still another preferred embodiment of the invention, the medicament fraction comprises albuterol base or sulfate.

In a further preferred embodiment of the invention, the medicament fraction comprises a combination of active ingredients, including, but not limited to, salmeterol, salmeterol xinafoate, or albuterol base (or sulfate) in combination with fluticasone propionate or fluticasone furoate.

In additional envisioned embodiments of the invention, the medicament fraction comprises medicament particles coated or co-precipitated with an additional excipient, by any suitable means. According to the invention, the additional excipient can be a surfactant, lubricant, polymer, amino acid, DPPC, polylactide, polysaccharide, targeting material, material having an opposite charge from the medicament, or any other material that provides beneficial properties to the aerosolibility, dispersability or therapeutic release profile of the medicament.

According to the invention, the medicament fraction is in the range of approximately 0.01 to 50%, preferably, 0.01 to 30%, more preferably, 0.01 to 20% by weight of the dry powder pharmaceutical composition. In a preferred embodiment of the invention, the medicament fraction is less than 10% by weight of the composition.

The medicament particles of the invention can be produced into appropriately sized particles by any suitable method of particle formation. The suitable methods include, but are not limited to, micronization, milling, spray drying and solvent/anti-solvent crystallization. In a preferred embodiment, micronization or milling are employed to produce the particles of the invention.

As indicated, the medicament particles of the invention preferably have an aerodynamic diameter no greater than 10 μm. The diameter of the medicament particles will, in accordance with the invention, range depending on factors such as particle composition and methods of synthesis.

Preferably, for local applications, the medicament particles have an aerodynamic diameter in the range of approximately 0.5 to 6 μm. More preferably, the medicament particles have an aerodynamic diameter in the range of approximately 2 to 6 μm. For systemic delivery, the medicament particles preferably have an aerodynamic diameter in the range of approximately 0.5 to 3 μm.

In a still further embodiment of the present invention, the medicament particles have a geometric diameter in the range of approximately 5 to 30 μm, wherein the tap density of the medicament particles is less than approximately 0.4 g/cm³. Preferably, the noted particles have an aerodynamic diameter in the range of approximately 1 to 5 μm.

As will be appreciated by one having ordinary skill in the art, the tap density, which has been used as a measure of the envelope mass density, is generally useful in characterizing the density of objects having irregular size and shape. Envelope density is generally determined by dividing the mass of an object by its volume, where the volume includes that of its pores and small cavities, but excludes interstitial spaces.

Non-Respirable Excipient Fraction

According to the invention, the non-respirable excipient fraction comprises at least one of the aforementioned excipients. The excipient is preferably biodegradable and biocompatible.

In a preferred embodiment of the invention, the non-respirable excipient fraction comprises at least one of the following excipients: pharmaceutical grades of carbohydrates (e.g., polysaccharides), amino acids, fatty acids, bio-compatible polymers or inorganic salts. More preferably, the non-reparable excipient fraction comprises lactose, mannitol, maltose, maltodextrins, dextrose, phenylalanine, leucine, glycine, diketopiperazine, calcium stearate, sodium stearyl fumarate, polylactic acid (PLA), polylactic-coglycolic acid (PLGA), a calcium salt and/or combinations thereof. Most preferably, the excipient fraction comprises mannitol.

As indicated, the non-respirable excipient fraction preferably comprises excipient particles having an aerodynamic diameter greater than approximately 10 μm and a geometric diameter greater than 30 μm. The non-respirable excipient particles are also preferably low density (i.e., tap density less than 0.8 g/cm³).

In a preferred embodiment of the invention, the non-respirable excipient particles have sufficient porosity (i.e., defining pores) to receive a portion of the medicament fraction and/or the respirable excipient fraction, discussed below. Alternatively, the non-respirable excipient particles may be fissured or solid walled, but hollow.

According to the invention, the non-respirable excipient particles can be produced using any conventional methods known in the art. The non-respirable excipient particles can also be fabricated or separated, for example by filtration, to provide a non-respirable excipient fraction with a preselected particle size distribution. For example, greater than 30%, 50%, 70%, or 80% of the particles in the non-respirable excipient fraction can have geometric diameter of at least 50 μm. The selected geometric diameter ranges within which a certain percentage of the non-respirable excipient particles must fall can be, for example, between about 30 to 300 μm, 60 to 160 μm, or 90 to 150 μm.

In a preferred embodiment of the invention, greater than 50%, more preferably, greater than 70% of the non-respirable excipient particles have a geometric diameter greater than 50 μm. In an alternative embodiment of the invention, greater than 90% of the non-respirable excipient fraction have a geometric diameter in the range of approximately 30 to 300 μm.

As will be appreciated by one having ordinary skill in the art, the use of larger particles is advantageous since the larger particles are able to flow more efficiently than smaller, aerosol particles, such as those currently employed for inhalation therapies. The presence of the higher proportion of the larger diameter particles in the non-respirable excipient fraction also enhances the delivery of the medicaments to the deep lung.

Respirable Excipient Fraction

The pharmaceutical compositions of the present invention can be further enhanced through the addition of a respirable sized excipient fraction comprising excipient particles with an aerodynamic diameter of 10 μm or less. More preferably, the respirable excipient particles have an aerodynamic diameter in the range of approximately 1 to 7 μm. In order to serve as efficient and safe medicament carriers, the respirable excipient particles are similarly preferably biodegradable and biocompatible, and optionally are capable of biodegrading at a controlled rate for delivery of a medicament.

According to the invention, the respirable excipient particles can be formed of any excipient that is suitable for pulmonary delivery. In a preferred embodiment of the invention, the excipient particles are formed by micronization or milling (i.e., wet or dry). Alternatively, such particles can be formed by spray drying, spray freeze drying, or other suitable processes.

According to the invention, the respirable excipient fraction can comprise any suitable excipient (and combinations thereof) including, but not limited to, sugars, lubricants, fatty acids, amino acids, stearates and their salts or esters, calcium salts and derivatives thereof, and biocompatible polymers. More preferably, the respirable excipient fraction comprises mannitol, lactose, phenylalanine, glycine, leucine, dibasic calcium phosphate, tribasic calcium phosphate, polylactic acid (PLA), polylactic-coglycolic acid (PLGA), diketopiperazine, calcium stearate, sodium stearyl fumarate, magnesium stearate and/or combinations thereof.

In a preferred embodiment of the invention, the respirable excipient fraction (i.e., micronized fraction) comprises in the range of 5% to 50% by weight of the dry powder pharmaceutical composition. In a still further embodiment, it is preferred that greater than 50% of the respirable excipient particles have an aerodynamic diameter in the range of approximately 1 to 8 μm.

As will be appreciated by one having ordinary skill in the art, the pharmaceutical compositions in accordance with the invention, can conveniently be filled into a bulk storage container, such as a multi-dose reservoir, or into unit dose containers such as capsules, cartridges or blister packs, which may be used with an appropriate pharmaceutical delivery device, for example, as described in GB 2041763, WO 91/13646, GB 1561835, GB 2064336, GB 2129691 or GB 2246299, which are incorporated by reference herein. The noted devices and aforementioned pharmaceutical delivery devices, containing a pharmaceutical composition in accordance with the invention, are deemed novel and, hence, form a further aspect of the invention.

The pharmaceutical compositions of the invention are particularly suitable for use with multi-dose reservoir-type devices in which the composition is metered, e.g., by volume from a bulk powder container into dose-metering cavities. The lower limit of powder delivery, which may be accurately metered from a multi-dose reservoir-type device, is typically in the range of 100 to 200 micrograms. The pharmaceutical compositions of the present invention are therefore particularly advantageous for highly potent and, hence, low dose medicaments that require a high ratio of excipient for use in a multi-dose reservoir-type device.

Administration of the pharmaceutical compositions of the present invention may be appropriate for the treatment of mild, moderate or severe acute or chronic symptoms or for prophylactic treatment. It will be appreciated that the precise dose administered will depend on the age and condition of the patient, the particular medicament used and the frequency of administration and will ultimately be at the discretion of the attendant physician.

Accordingly, in one embodiment of the invention, the invention includes the delivery of a dry powder pharmaceutical composition of the invention to the pulmonary system of a patient comprising: (i) providing a pharmaceutical delivery device containing a dry powder pharmaceutical composition comprising a medicament fraction and at least 50% of a non-respirable excipient fraction, the medicament fraction comprising medicament particles having an aerodynamic diameter no greater than 10 μm and the non-respirable excipient fraction comprising excipient particles having an aerodynamic diameter greater than 10 μm and a geometric diameter greater than 30 μm; (ii) introducing an air flow within said delivery device; (iii) aerosolizing the dry powder pharmaceutical composition into the air flow; (iv) dispersing the aerosolized pharmaceutical composition into a plume; (v) emitting the aerosolized pharmaceutical composition from the delivery device; and (vi) delivering the plume to the pulmonary system of the patient.

In an alternative embodiment of the method of the present invention, the delivery device further comprises a source of aerosolization energy that is independent of patient inhalation effort. The noted method further includes the step of releasing this aerosolization energy to create air flow which aerosolizes the dry powder pharmaceutical composition.

In a preferred embodiment of the invention, 40% or greater of the dry powder pharmaceutical composition is emitted from the delivery device. In a further embodiment of the invention, the fine particle fraction (e.g., medicament fraction) of the emitted dose is 40% or greater.

The invention further includes processes for forming the unique pharmaceutical compositions and the products produced thereby. In one embodiment, the process for forming the pharmaceutical compositions of the invention preferably comprises (i) providing medicament particles having an aerodynamic diameter no greater than 10 μm; (ii) providing first excipient particles having an aerodynamic diameter no greater than 10 μm; (iii) providing second excipient particles having an aerodynamic diameter greater than 10 μm and a geometric diameter greater than 30 μm; (iv) preblending the first and second excipient particles to form an excipient composition; and (v) blending the medicament particles and excipient composition.

In a preferred embodiment of the invention, the second excipient particles include defining pores. During the pre-blending step, a portion of the first excipient particles are disposed in the defining pores of the second excipient particles.

In an additional embodiment of the invention, the process for forming the pharmaceutical compositions of the invention comprises (i) providing medicament particles having an aerodynamic diameter no greater than 10 μm; (ii) providing first excipient particles having an aerodynamic diameter no greater than 10 μm; (iii) providing second excipient particles having an aerodynamic diameter greater than 10 μm and a geometric diameter greater than 30 μm; (iv) preblending the medicament particles and second excipient particles to form a medicament/excipient composition; and (v) blending the first excipient particles and medicament/excipient composition.

In a preferred embodiment, the second excipient particles include defining pores. During the pre-blending step, a portion of the medicament particles are disposed in the defining pores of the second excipient particles.

In a further embodiment of the invention, the process for forming the pharmaceutical compositions of the invention comprises (i) providing medicament particles having an aerodynamic diameter no greater than 10 μm; (ii) providing first excipient particles having an aerodynamic diameter no greater than 10 μm; (iii) providing second excipient particles having an aerodynamic diameter greater than 10 μm and a geometric diameter greater than 30 μm; (iv) preblending the medicament particles and first excipient particles to form a medicament/excipient composition; and (v) blending the second excipient particles and medicament/excipient composition.

In a preferred embodiment of the invention, the second excipient particles include defining pores. During the blending step, a portion of the medicament/excipient composition is disposed in the defining pores of the second excipient particles.

EXAMPLES

The examples that are set forth herein are for illustrative purposes only and are not meant to limit the scope of the invention(s) in any way.

The following materials were used in the examples recited below. Unless otherwise indicated, commercially available components or apparatus were employed.

Materials
Non-Respirable Excipients
Milled lactose: $D_{50}$—50-70 μm
Sieved lactose: $D_{50}$—150-170 μm (air jet sieved)
Sieved mannitol: $D_{50}$—160-180 μm (air jet sieved)
Pearlitol 100: spray dried mannitol-$D_{50}$—90-110 μm
Pearlitol 200: spray dried mannitol-$D_{50}$—130-160 μm
Pearlitol 70: spray dried mannitol-$D_{50}$—65-90 μm
Note: Each of the non-respirable excipients exhibited an aerodynamic diameter≧10 μm.
Respirable Excipients
Spray dried glycine: $D_{50}$—6-8 μm
Spray dried mannitol (coarse): $D_{50}$—6-8 μm
Spray dried mannitol (fine): $D_{50}$—2-3 μm
Milled mannitol: $D_{50}$—18-22 μm
Micronized mannitol: $D_{50}$—1-3 μm
Micronized glycine: $D_{50}$—2-4 μm
Micronized phenylalanine: $D_{50}$—1-3 μm
Micronized disclaim phosphate: $D_{50}$—1-3 μm
Tricalcium Phosphate: $D_{50}$—5-7 μm
Methods
Preblending: as used in the following examples, preblending entailed combining a coarse excipient fraction with a fine excipient or medicament fraction and blending in a low shear or high shear blending procedure for a given period of time, under specified conditions to achieve a homogenous first composition. Unless otherwise indicated, the preblending procedure employed comprised sandwiching the fine component between the two halves of coarse excipient and blending for 10 minutes at 90 rpm using a Turbula T2 blender (commercially available from Glen Mills Inc., Clifton, N.J.).

Blending: as used in the following examples, blending entailed combining the homogeneous first composition with a further component (i.e., medicament or fine excipient) in a low shear or high shear blending procedure for a given period of time, under specified conditions to achieve a homogenous second composition. Unless otherwise indicated, the blending procedure employed herein comprised sandwiching the further component between the two halves of preblend and blend for 10 minutes at 90 rpm using a Turbula T2 blender.

Cascade Impaction (CI): The blends were introduced into a multi-stage cascade impactor by passing a stream of gas over the substrate recess. This allows the blend to be aerosolized and introduced into the impactor. A reduced cascade impactor (i.e., stages 3-6 removed) is used unless otherwise described. The mass of the material deposited on each stage of the impactor was evaluated by high pressure liquid chromatography. The CI data was obtained at 28.3 l/min.

Excipient Flow Properties

The % compressibility of the excipient (i.e., lactose) powder was determined via a Hosokawa PT-N powder flow tester, which provides a direct measure of tap density and bulk density. The following % compressibility equation was also employed, $$\% \text{ compressibility} = (\text{tap density} - \text{bulk density}/\text{tap density}) \times 100 \qquad \text{Eq. 1}$$

Referring to Table I, there is shown a comparison of a narrow distribution of lactose powder. As illustrated in Table I, the % compressibility of the lactose powder was relatively low, which, as will be appreciated by one having ordinary skill in the art, is generally indicative of enhanced flow characteristics (e.g., ↓% compressibility=↑flow). The lactose powder also exhibited a much lower bulk and tap density due to the porous nature of the material.

TABLE I

| Sample | Bulk Density (%) | Tap Density (%) | % Compressibility | Angle of Repose (°) |
|---|---|---|---|---|
| Pearlitol 100 | 0.479 | 0.582 | 17.6 | 37.3 |
| Pearlitol 200 | 0.446 | 0.515 | 13.4 | 35.7 |
| Lactose AJS* | 0.683 | 0.907 | 24.7 | 38.6 |

*through a 105 μm sieve, retained on a 25 μm sieve

Examples 1-2

Effect of Fines Size 100 gm blends of fluticasone propionate ("FP") and excipient were prepared as shown in Table II.

TABLE II

| Blend | Active | Fine Excipient | Coarse Excipient |
|---|---|---|---|
| 1 | 10 gm FP | 18 gm spray dried mannitol (fine) | 72 gm of Pearlitol 100 |
| 2 | 10 gm FP | 18 gm milled mannitol | 72 gm of Pearlitol 100 |

1 mg of each blend was then aerosolized into the cascade impactor at 28.3 l/min. Referring to Table III, each data point represents an individual blister. Note: three (3) blisters were employed to demonstrate the variability in performance.

TABLE III

| Blend | Device and Blister (%) | Throat (%) | Emitted (%) | % Total FPM (2-F) | % Emitted FPM (2-F) |
|---|---|---|---|---|---|
| 1 | 12.4 (11.9-13.0) | 22.1 (21.0-22.8) | 87.6 (87.0-88.1) | 54.4 (53.6-54.9) | 62.0 (61.6-62.6) |
| 2 | 10.1 (9.1-11.8) | 26.7 (26.6-26.9) | 89.9 (88.2-90.9) | 46.8 (46.6-47.0) | 52.1 (51.4-53.2) |

The data indicates that different size fines can be employed in conjunction with an aerodynamically light carrier (e.g., porous excipient) to give consistently high FPM performance.

Examples 3-7

Effect of Formulation Variables 100 gm blends were prepared as shown in Table IV. As indicated in Table V, Blends 3 and 6 were subjected to a preblend. Blends 4 and 5 were not subjected to a preblend. All three components were, however, mixed in a single blending step.

TABLE IV

| Blend | Active | Fine Excipient | Coarse Excipient |
|---|---|---|---|
| 3 | 1 gm FP | 40 gm spray dried mannitol (fine) | 59 gm of Pearlitol 100 |
| 4 | 10 gm FP | 40 gm spray dried mannitol (fine) | 50 gm of Pearlitol 100 |
| 5 | 1 gm FP | 10 gm spray dried mannitol (fine) | 89 gm of Pearlitol 100 |
| 6 | 10 gm FP | 10 gm spray dried mannitol (fine) | 80 gm of Pearlitol 100 |

1 mg of each blend was then aerosolized into the impactor at 28.3 l/min. Each data point in Table V similarly represents an individual blister.

TABLE V

| Blend | Preblend | Device and Blister (%) | Throat (%) | Emitted (%) | % Total FPM (2-F) | % Emitted FPM (2-F) |
|---|---|---|---|---|---|---|
| 3 | yes | 14.7 (12.8-17.5) | 24.2 (20.4-26.6) | 85.3 (82.3-87.8) | 42.5 (41.2-43.6) | 49.8 (47.7-51.8) |

TABLE V-continued

| Blend | Preblend | Device and Blister (%) | Throat (%) | Emitted (%) | % Total FPM (2-F) | % Emitted FPM (2-F) |
|---|---|---|---|---|---|---|
| 4 | no | 16.4 (15.0-18.3) | 24.5 (21.5-27.6) | 83.6 (81.7-85.0) | 46.4 (44.4-47.7) | 55.6 (52.8-58.4) |
| 5 | no | 14.2 (9.5-20.0) | 21.2 (19.8-23.8) | 85.8 (80.0-90.5) | 25.1 (22.3-29.5) | 29.2 (27.6-32.6) |
| 6 | yes | 13.7 (13.6-13.8) | 30.3 (29.1-31.1) | 86.3 (86.2-86.4) | 42.9 (42.2-43.4) | 49.7 (49.0-50.7) |

The noted data thus indicates that at low blend concentrations, higher fines and preblending are important to achieve high FPM performance.

Examples 8-11

Effect of High Shear Blending 100 gm blends were prepared by using a Waring blender at low speed for 90 seconds. As indicated in Table VII, blends 9 and 11 were subjected to a preblend, while blends 8 and 10 were not. All three components were, however, mixed in a single blending step.

TABLE VI

| Blend | Active | Fine Excipient | Coarse Excipient |
|---|---|---|---|
| 8 | 1 gm FP | 40 gm spray dried mannitol (fine) | 59 gm of Pearlitol 100 |
| 9 | 10 gm FP | 40 gm spray dried mannitol (fine) | 50 gm of Pearlitol 100 |
| 10 | 10 gm FP | 10 gm spray dried mannitol (fine) | 89 gm of Pearlitol 100 |
| 11 | 1 gm FP | 10 gm spray dried mannitol (fine) | 80 gm of Pearlitol 100 |

1 mg of each blend was then aerosolized into the impactor at 28.3l/min. Referring to Table VII, there is shown the FPM performance for the noted blends. Each data point represents an individual blister.

TABLE VII

| Blend | Blending | Device and Blister (%) | Throat (%) | Emitted (%) | % Total FPM (2-F) | % Emitted FPM (2-F) |
|---|---|---|---|---|---|---|
| 8 | no preblend | 15.9 (14.3-18.8) | 18.0 (17.3-18.9) | 84.1 (81.2-85.7) | 46.5 (44.7-47.6) | 55.2 (54.8-55.8) |
| 9 | preblend | 15.8 (14.1-18.0) | 23.5 (22.2-24.9) | 84.2 (82.0-85.9) | 45.6 (45.2-46.3) | 54.1 (53.3-55.2) |
| 10 | no preblend | 16.5 (15.7-18.0) | 21.6 (20.4-22.5) | 83.5 (82.0-84.3) | 39.6 (38.6-40.6) | 47.4 (47.0-48.2) |
| 11 | preblend | 15.7 (14.8-16.2) | 16.7 (15.7-18.2) | 84.3 (83.5-85.2) | 50.7 (50.0-51.5) | 60.1 (58.6-61.4) |

The noted data thus indicates that the blending method and formulation composition can further enhance FPM performance.

Example 12

Effect of Coarse Carrier Size

A 100 gm blend was prepared having the composition shown in Table VIII.

TABLE VIII

| Blend | Active | Fine Excipient | Coarse Excipient |
|---|---|---|---|
| 12 | 10 gm FP | 20 gm spray dried mannitol (fine) | 70 gm of Pearlitol 200 |

1 mg of the blend was then aerosolized into the impactor at 28.3l/min. As indicated in Table IX, a larger grade of the coarse aerodynamically light carrier provides comparable results to those observed with Pearlitol 100.

TABLE IX

| Blend | Emitted (%) | % Total FPM (2-F) | % Emitted FPM (2-F) |
|---|---|---|---|
| 12 | 88.2 (86.0-89.8) | 59.8 (59.6-60.0) | 68.0 (66.9-69.3) |

Examples 13-15

Effect of Active 100 gm blends were prepared as shown in Table X.

TABLE X

| Blend | Drug | Fine Excipient | Coarse Excipient |
|---|---|---|---|
| 13 | 10 gm Albuterol | 20 gm spray dried mannitol (fine) | 70 gm of Pearlitol 200 |
| 14 | 10 gm Salmeterol | 20 gm spray dried mannitol (fine) | 70 gm of Pearlitol 200 |

1 mg of each blend was then aerosolized into the impactor at 28.3 l/min. As indicated in Table XI, good FPM performance and emitted dose can be achieved from a range of medicaments.

TABLE XI

| Blend | Emitted (%) | % Total FPM (2-F) | % Emitted FPM (2-F) |
|---|---|---|---|
| 13 | 92.5 | 64.7 | 70.0 |
|  | (91.0-93.7) | (64.8-66.5) | (67.6-73.1) |
| 14 | 95.1 | 80.2 | 84.3 |
|  | (94.4-95.6) | (80.0-80.3) | (83.9-85.1) |

Examples 15-16

Effect of Active Concentration 2 gm blends were prepared as shown in Table XII.

TABLE XII

| Blend | Active | Fine Excipient | Coarse Excipient |
|---|---|---|---|
| 15 | .02 gm Salmeterol | .4 gm spray dried mannitol (fine) | 1.58 gm of Pearlitol 100 |
| 16 | 0.2 gm Salmeterol | .4 gm spray dried mannitol (fine) | 1.4 gm of Pearlitol 200 |

1 mg of each blend was then aerosolized into the impactor at 28.3 l/min. In these examples, a full cascade impactor was used in place of the normal reduced cascade impactor.

TABLE XIII

| Blend | Device and Blister (%) | Throat (%) | Emitted (%) | % Total FPM (2-F) | % Emitted FPM (2-F) |
|---|---|---|---|---|---|
| 15 | 8.5 | 11.5 | 91.6 | 59.3 | 64.8 |
|  | (7.8-8.9) | (11.2-11.9) | (91.1-92.2) | (56.5-61.8) | (61.9-67.8) |
| 16 | 4.8 | 10.2 | 95.2 | 77.7 | 81.6 |
|  | (3.5-5.5) | (9.7-11.2) | (94.5-96.5) | (74.9-79.8) | (79.2-82.9) |

Referring to Table XIII, the noted data indicates that good, consistent FPM performance and emitted dose performance can be obtained at a lower medicament concentration.

Examples 17-23

Effect of Fine Carrier Type 20 gm blends were prepared as shown in Table XIV.

TABLE XIV

| Blend | Drug | Fine Excipient | Coarse Excipient |
|---|---|---|---|
| 17 | 2 gm Albuterol | 4 gm spray dried mannitol (coarse) | 14 gm of Pearlitol 200 |
| 18 | 2 gm Albuterol | 4 gm micronized mannitol | 14 gm of Pearlitol 200 |
| 19 | 2 gm Albuterol | 4 gm spray dried glycine | 14 gm of Pearlitol 200 |
| 20 | 2 gm Albuterol | 4 gm micronized glycine | 14 gm of Pearlitol 200 |
| 21 | 2 gm Albuterol | 4 gm micronized phenylalanine | 14 gm of Pearlitol 200 |
| 22 | 2 gm Albuterol | 4 gm milled tricalcium phosphate | 14 gm of Pearlitol 200 |
| 23 | 2 gm Albuterol | 4 gm micronized dicalcium phosphate | 14 gm of Pearlitol 200 |

1 mg of each blend was then aerosolized into the impactor at 28.3 l/min. Referring to Table XV, there is shown the FPM performance of each blend.

TABLE XV

| Blend | Emitted (%) | % Total FPM (2-F) | % Emitted FPM (2-F) | % Compressibility |
|---|---|---|---|---|
| 17 | 88.7 | 62.6 | 70.6 | 33.3 |
|  | (86.2-91.2) | (61.4-63.9) | (70.1-71.2) |  |
| 18 | 94.6 | 67.5 | 71.3 | 16.6 |
|  | (93.7-95.4) | (66.6-68.4) | (71.0-71.6) |  |
| 19 | 93.6 | 58.9 | 62.9 | 26.4 |
|  | (93.3-94.0) | (53.3-64.5) | (56.7-69.2) |  |
| 20 | 94.2 | 54.1 | 57.4 | 22.3 |
|  | (93.4-94.9) | (50.7-57.4) | (54.3-60.5) |  |
| 21 | 87.5 | 68.5 | 78.3 | 23.0 |
|  | (85.7-89.5) | (67.5-69.5) | (77.9-78.7) |  |
| 22 | 91.0 | 56.6 | 62.3 | 18.7 |
|  | (88.8-93.1) | (54.0-59.2) | (58.0-66.6) |  |
| 23 | 82.6 | 65.8 | 78.9 | 18.1 |
|  | (80.8-85.9) | (63.5-68.1) | (78.6-79.2) |  |

The data set forth in Table XV indicates that a range of fine excipients can be employed to provide good FPM performance and emitted dose performance. In addition, the powder flow properties can be modified through the size/shape or type of fine excipient. Accordingly, powder flow properties can be changed to suit the processes used during the manufacturing process.

Examples 24-26

Effect on Stability

The blends shown in Table XVI were stored at 40° C./75% RH for 3 days in unsealed blisters to investigate the effect of humidity on powder storage.

TABLE XVI

| Blend | Active | Fine Excipient | Carrier |
|---|---|---|---|
| 24 | 10 gm FP | 20 gm spray dried mannitol (fine) | 70 gm Pearlitol 200 |
| 25 | 0.4 gm FP | NA | 99.6 gm milled lactose |
| 26 | 2 gm FP | NA | 98 gm milled lactose |

Referring to Table XVII, the stability data indicates that the low density excipient based formulation has significantly better stability in open blisters than the blends typically employed in MDPIs.

TABLE XVII

| Blend | FPM Before Storage | FPM After Storage | Difference | % DROP |
|---|---|---|---|---|
| 24 | 54.4 (53.5-55.6) | 53.7 (52.7-55.1) | 0.7 | 1.3 |
| 25 | 24.4 (20.3-27) | 10.3 (8.0-11.3) | 14.1 | 58 |
| 26 | 27.8 (25.7-29.2) | 15.9 (13.5-17.4) | 11.9 | 43 |

Examples 27-30

20 gm coarse carrier blends were prepared as shown in Table XVIII.

TABLE XVIII

| Blend | Active | Fine Excipient | Carrier |
|---|---|---|---|
| 27 | 2 gm FP | 4 gm spray dried mannitol | 14 gm Pearlitol 70 |
| 28 | 2 gm FP | 4 gm micronized phenylalanine | 14 gm Pearlitol 70 |
| 29 | 2 gm Albuterol | 4 gm spray dried mannitol | 14 gm Pearlitol 70 |
| 30 | 2 gm Albuterol | 4 gm micronized phenylalanine | 14 gm Pearlitol 70 |

1 mg of each blend was then aerosolized into the impactor at 28.31/min. Referring now to Table XIX, it can be seen that similar results are obtained with Pearlitol 70 as obtained with Pearlitol 100 and 200.

TABLE XIX

| Blend | Emitted (%) | % Total FPM (2-F) | % Emitted FPM (2-F) |
|---|---|---|---|
| 27 | 79.1 (76.2-81.9) | 40.6 (40.4-40.7) | 51.4 (49.7-53.1) |
| 28 | 82.1 (78.5-85.6) | 56.2 (53.8-56.2) | 68.5 (68.5-68.6) |
| 29 | 87.3 (82.5-92.1) | 57.2 (55.9-58.4) | 65.6 (63.4-67.8) |
| 30 | 86.7 (84.1-89.4) | 72.4 (64.8-80.1) | 83.3 (77.1-89.5) |

Throughout the claims which follow, unless the context requires otherwise, the word "comprise", and variations such as "comprises" and "comprising", will be understood to imply the inclusion of a stated integer or step or group of integers but not to the exclusion of any other integer or step or group of integers or steps.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A pharmaceutical composition obtained by providing medicament particles having an aerodynamic diameter no greater than 10 µm,
   providing first excipient particles having an aerodynamic diameter no greater than 10 µm,
   providing second excipient particles and having an aerodynamic diameter greater than 10 µm and a geometric diameter from 90 µm to 150 µm,
   preblending said medicament particles and said first excipient particles to form a medicament/excipient composition, and wherein a portion of said first excipient particles are disposed in said defining said pores during said pre-blending step, and
   blending said second excipient particles and said medicament/excipient composition;
   wherein said pharmaceutical composition is present in the form of a dry powder.

2. The pharmaceutical composition according to claim 1, wherein the medicament particles comprise a medicament selected from the group consisting of an analgesic, anginal preparation, antiallergic, antibiotic, antiinfective, antihistamine, anti-inflammatory, antitussive, bronchodilator, $\alpha_4$ integrin inhibitor, diuretic, anticholinergic, adenosine 2a agonists, hormones, xanthine, vaccine, therapeutic protein, peptide, and combinations thereof.

3. The pharmaceutical composition according to claim 1, wherein the first excipient particles comprise at least one excipient selected from the group consisting of sugars, lubricants, fatty acids, amino acids, stearates and their salts or esters, calcium salts, derivatives thereof, and biocompatible polymers.

4. The pharmaceutical composition according to claim 1, wherein the first excipient particles comprise at least one excipient selected from the group consisting of mannitol, lactose, phenylalanine, glycine, leucine, dibasic calcium phosphate, tribasic calcium phosphate, polylactic acid (PLA), polylactic-coglycolic acid (PLGA), diketopiperazine, calcium stearate, sodium stearyl fumarate, and magnesium stearate.

5. The pharmaceutical composition according to claim 1, wherein the second excipient particles comprise at least one excipient selected from the group consisting of carbohydrates, amino acids, fatty acids, bio-compatible polymers, and inorganic salts.

6. The pharmaceutical composition according to claim 1, wherein the second excipient particles comprise at least one excipient selected from the group consisting of lactose, mannitol, maltose, maltodextrins, dextrose, phenylalanine, leucine, glycine, diketopiperazine, calcium stearate, sodium stearyl fumarate, polylactic acid (PLA), polylactic-coglycolic acid (PLGA), and a calcium salt.

7. A process for producing a pharmaceutical composition, comprising the steps of:
   providing medicament particles having an aerodynamic diameter no greater than 10 µm;
   providing first excipient particles having an aerodynamic diameter no greater than 10 µm;
   providing second excipient particles including defining pores and having an aerodynamic diameter greater than 10 µm and a geometric diameter from 90 µm to 150 µm;
   preblending said first and second excipient particles to form an excipient composition, wherein a portion of said first excipient particles are disposed in said pores; and
   blending said medicament particles and said excipient composition to form a pharmaceutical composition present in the form of a dry powder.

* * * * *